United States Patent [19]
Leon

[11] Patent Number: 5,725,372
[45] Date of Patent: Mar. 10, 1998

[54] TOOTH SHADE GUIDE

[76] Inventor: Joel Leon, 326 Round Hill Rd., Greenwich, Conn. 06830

[21] Appl. No.: 618,578

[22] Filed: Mar. 20, 1996

[51] Int. Cl.⁶ ............................... A61C 19/10
[52] U.S. Cl. ............................. 433/26; 206/83
[58] Field of Search .................. 433/26; 206/83

[56] References Cited

U.S. PATENT DOCUMENTS

| | | | |
|---|---|---|---|
| 1,518,608 | 12/1924 | Short | 206/83 |
| 2,479,543 | 8/1949 | Russell | 433/26 |
| 4,115,922 | 9/1978 | Alderman | 206/83 |
| 4,207,678 | 6/1980 | Jeannette | 433/26 |
| 4,620,841 | 11/1986 | Farrell et al. | 433/26 |
| 4,810,193 | 3/1989 | Wieder | 433/26 |
| 4,978,296 | 12/1990 | Antons et al. | 433/26 |
| 5,066,227 | 11/1991 | Pozzi | 433/26 |
| 5,240,414 | 8/1993 | Thompson | 433/26 |
| 5,498,157 | 3/1996 | Hall | 433/26 |
| 5,588,834 | 12/1996 | Resk et al. | 433/26 |

*Primary Examiner*—Ralph Lewis
*Attorney, Agent, or Firm*—Alfred E. Miller

[57] ABSTRACT

A tooth shade guide having the general configuration of the artificial tooth to be placed in a patient's mouth, and of the same materials and thickness as the artificial tooth. The tooth shade guide can be temporarily held in place in the exact location the artificial tooth will occupy in order to observe the tooth shade match vis-avis the adjacent teeth.

3 Claims, 2 Drawing Sheets

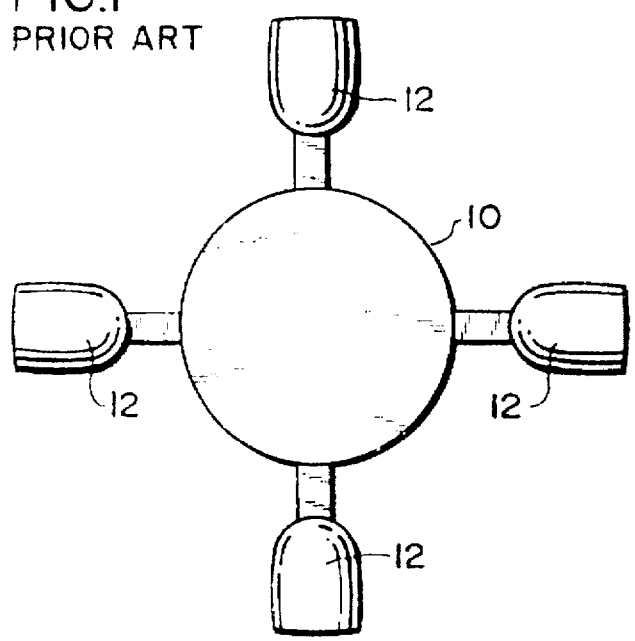
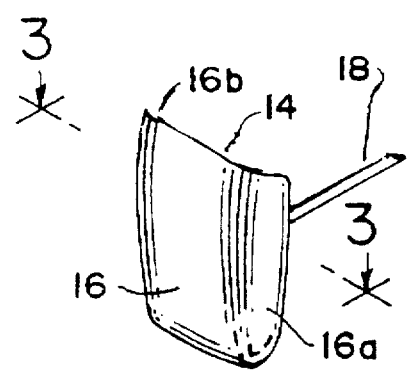
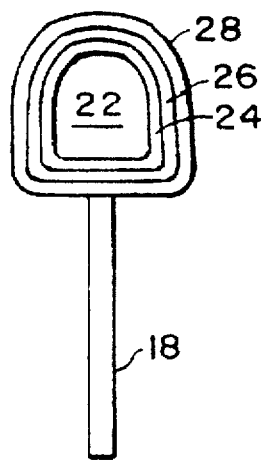
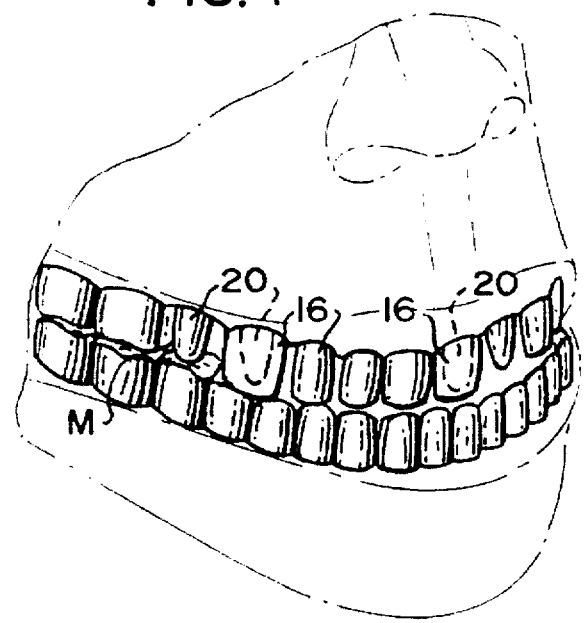

TOOTH SHADE GUIDE

BACKGROUND OF THE INVENTION

This invention relates to a tooth shade guide for use in preparing artificial teeth, such as crowns and bridges, that will accurately match a patient's natural teeth.

Matching the color of natural teeth is a multi-factorial problem. Many qualities impact the color of teeth including hue (i.e. color), chroma (the intensity or concentration of color), surface texture effecting whiteness-grayness value, the light source (e.g. white light, etc.), reflection and absorption, the presence of primary, secondary and complementary colors. Also important to the color of teeth are additive and substractive color effects and metamerism. Additive and substractive color effects result when the mixing of colors produces a combination hue with increased or decreased value. Metamerism results from different light sources. For example, an object may reflect more red than another object. When there is no red range in the light source, these objects will appear the same. When viewed under a light source containing red, they will appear different.

Natural teeth are made up of layers. The outer layer of a natural tooth is enamel at the crown and cementin at the root. Under the enamel is a layer of dentin. Under the dentin is another layer of dentin known as secondary dentin. This layering results in additive, subtractive and metameric color effects that are very difficult to recreate in an artificial tooth. For example, each layer of a natural tooth may have varying amounts of color and translucency that impact the appearance of the tooth. The color qualities of adjacent teeth can also impact the ultimate appearance of a tooth.

Artificial teeth can be similarly constructed of layers. In general, a metal coping is coated with a layer of opaque, which in turn is coated with a layer of porcelain, dentin or body which is an artificial tooth, such as a crown covered by a layer of enamel or incisal porcelain to produce. In order to closely match the coloration of a natural tooth, an artificial tooth must have its colors and translucency in the same layers and amounts as the natural tooth.

Commercial tooth shade guides used for the selection of the color of artificial teeth have generally been comprised of a series of guides in various shades having the general shape of the front surface of a tooth with each guide permanently attached to a handle which the dentist holds next to the tooth or teeth to be matched. U.S. Pat. No. 3,964,167 shows a shade guide that is pivotably mounted on a handle such that the shade guide can tilt relative to the handle. The color match is then made by a trial and error process of holding up various shade guides to the tooth or teeth to be matched and selecting the color that most closely approximates the tooth or teeth to be matched.

A major drawback of these guides is that they cannot always be positioned in the patient's mouth in the position that the artificial tooth will eventually occupy, i.e. over a prepared tooth. Due to the complex optical properties of teeth, the position of a tooth in the mouth is very important to its ultimate appearance. Another drawback of these guides is that they must be held up by the dentist, further distorting the light reaching the tooth and thus, the ultimate appearance of the tooth. A further drawback of these tooth shade guides is that they are not made in the same way and of the same materials as the artificial replacement tooth. Because the optical properties of an object vary according to the material and physical structure of the object, a tooth shade guide that is not constructed like an artificial tooth or comprised of the identical materials from which an artificial tooth will be made, will not have the same optical properties as the artificial replacement tooth it is intended to match.

Another drawback of the prior construction is that the layers of material of these guides is much thicker than that of the final crown.

Still another drawback of the prior construction is that the back portion does not simulate the construction of the final restoration and this affects the appearance of the sides of the front of the guides.

SUMMARY OF THE INVENTION

In general, the invention features a tooth shade guide which is configured so that it can be positioned over a prepared tooth or pontic area in a patient's mouth in the position that an artificial tooth will eventually occupy.

In another aspect, the invention features a tooth shade guide that is comprised of the same materials from which the artificial replacement tooth will be made and is constructed of layers in the same manner and the same thickness as the artificial replacement tooth.

Another aspect of the present invention is to construct a ceramo-metal tooth shade guide in which the metal is covered by a layer of opaque porcelain which, in turn, is covered by a layer of dentin porcelain and this layer is covered by a layer of incisal or enamel porcelain. This arrangement permits one to have the colors and the translucency of the ceramo-metal restoration in the same places and to the same extent as the natural dentition. On the other hand, the prior art ceramo-metal guides do not match the porcelain obtained from dental laboratories, who, in turn, purchase the material from the manufacturers. Thus, an effective guide must be constructed for each brand name porcelain.

In another aspect, the invention features a plurality of such tooth shade guides in varying sizes corresponding to different types of teeth such as incisors, premolars and molars.

In another aspect, the invention features a plurality of such tooth shade guides in varying shades corresponding to common colors of natural teeth.

Another feature of the present invention is that my tooth shade guide can be temporarily held in place with a temporary tacking medium, or a clear, light cured temporary material that never sets hard so that it can be easily removed after observing the same in the proper position.

In another aspect, the invention features a handle portion configured to fit into a holder for storage and ease of placement that is not visible when the guide is in place in the mouth.

In another aspect, the invention features a holder for a set of such tooth shade guides for easy storage.

Other features and advantages of the invention will be apparent from the following description of the preferred embodiment and from the claims. The concept of the invention also applies to the guides made of other materials. This may or may not have metal backings.

BRIEF DESCRIPTION OF THE DRAWINGS

FIG. 1 is a front elevational view of a prior art tooth shade guide.

FIG. 2 is a perspective view of a tooth shade guide constructed in accordance with the present invention.

FIG. 3 is a view taken through the lines 3—3 of FIG.2.

FIG. 4 is a perspective view of a patient's mouth showing the tooth shade guide in the position that the artificial tooth will eventually occupy.

DESCRIPTION OF THE PREFERRED EMBODIMENTS

Figure 5:
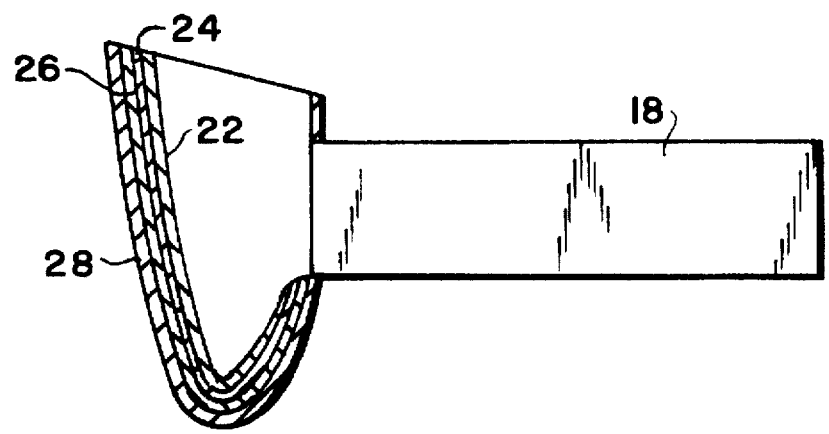
FIG. 5 is a view partly in section and partly in elevation of the tooth shade guide.

FIG. 1 shows a prior art enamel tooth shade guide arranged on a circular hub or holder 10 having radial spokes 12 of the guide provided with opaque and body porcelain layers, and having four different shades. The spokes of the guide are rotated in the area where the artificial tooth will occupy next to the adjacent teeth and as close as possible in order to determine a proper color match. The shade guides of choice for a porcelain selection are Vita Lumin standard. The disadvantage of the prior art shade guide devices have been discussed hereinbefore.

Referring now to FIGS. 2–5, the tooth shade guide of the present invention referred to generally by the reference numeral 13 is adapted to fit over a post or anchor in a patient's mouth by a dentist and occupies a position that the artificial tooth will eventually occupy. Preferably, the tooth shade guide 14 has at least a front surface 16 having the general configuration of an artificial tooth which is not a complete tooth since there is no rear tooth simulated surface but instead a handle 18 attaches to the rear surface area. The tooth shade guide shown in the drawings is preferably comprised of the same materials from which the artificial replacement tooth will be made, as described more fully hereinbelow.

Referring now to FIGS. 3 and 5, a cross section of the tooth shade guide is shown in which a post 20 (FIG. 4) appears in the location that the artificial tooth will occupy, the present tooth shade guide place has a metal coping 22 surrounding the post and a layer of opaque 24 is shown surrounding the metal coping. A further layer of dentin 26 is further applied to the opaque, and finally the exterior layer of the tooth shade guide is fabricated of enamel 28. Thus, it should be apparent that the various layers of the tooth shade guide are precisely the same as the layers in a ceramo-metal restoration for an artificial tooth. It should also be apparent that the thickness of the layers in the tooth shaped guide is the same thickness as that of the ceramo-metal restoration. Thus, an accurate conception of what the ceramo-metal restoration will look like in the proper position in the patient's mouth can be determined with the use of the tooth shade guide.

It should be noted that the common ceramo-metal tooth shade guides presently in use by the dental profession do not match the porcelain that the laboratories buy from the manufacturers. Thus, a custom guide must be constructed for each brand name porcelain so that a true color match can be obtained. The guides used to match composite or acrylic materials are made of the same materials and are partially layered correctly but they are too thick, and will not fit over a dental preparation. Thus, it should be apparent that conventional shade guides do not have the same color as the powders they purchase from the manufacturer or distributor.

Referring to FIG. 4, the tooth shade guide 13 can be positioned over a post in a patient's mouth M by a dentist so that it occupies the position that an artificial tooth will eventually occupy. Preferably, tooth shade guide 13 has at least a wrap around surface on substantially three surfaces 16, 16a and 16b and gives the appearance of a complete crown. A critical feature, therefore, is to permit the guide to wrap around the prepared tooth from the buccal to the lingual areas of the patient and is of the same thickness as the final restoration. The tooth shade guide shown in FIGS. 2 and 3 are preferably comprised of the same materials from which the artificial replacement tooth will be made, as described more fully below.

The tooth shade guide after being fabricated is temporarily held in place in the eventual location the artificial tooth will occupy by a temporary tacking medium (not shown), or a clear, light cured temporary material that never permanently sets, so that the shade appearance of the end result artificial tooth can be observed and analyzed in it's exact location. Thereafter, the shade guide can be easily removed.

It should be evident that if a more precise guide is constructed for a particular patient different color and opacities of porcelain can be used to modify the hue in different areas, such as the neck of the tooth may have a darker color applied than the body of the tooth. Moreover, surface stains can be applied in order to achieve a precise match. It should be evident that the guide can be constructed to satisfy any standard.

The metal layer may be constituted of different types of metal. However, since the oxide of different metals affects the color of the opaque layer in different ways, the shade guide can be constructed of any metal that is used to fabricate the final crown.

The tooth shade guide shown in FIG. 2 is intended to be one of a set of tooth shade guides in varying shades and sizes. Preferably, the varying shades correspond to common colors of natural teeth. The varying sizes preferably correspond to different types of teeth such as incisors, pre-molars, molars, etc.

Figure 6:
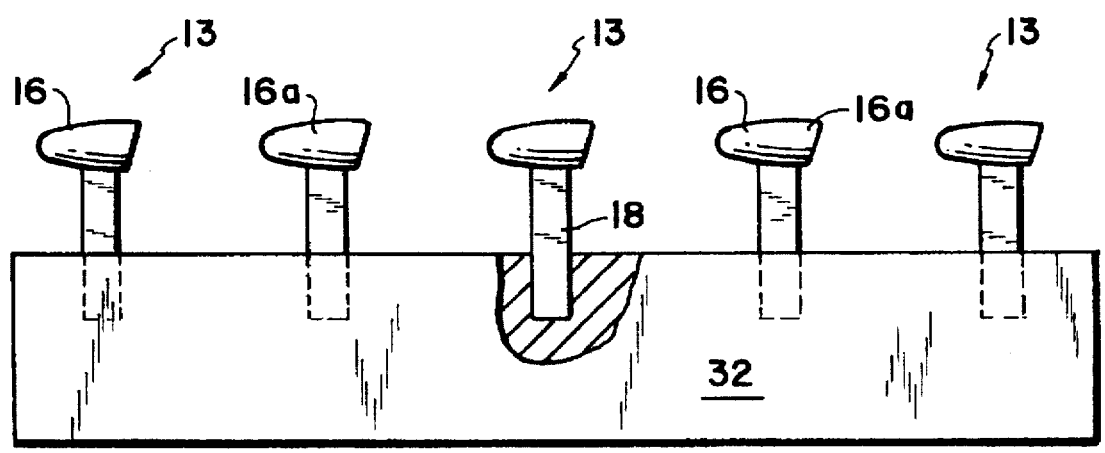
FIG. 6 is a perspective view of a holder for a set of tooth shade guides.

Referring to FIGS. 2 and 5, the tooth shade guide handle portion 18 is attached to the rear of the device which the dentist may use to position the guide over a post in a patient's mouth or in an open area between teeth in a patients mouth. The handle portion allows a dentist to use the tooth shade guide without touching the colored portion of the guide. The handle portion also allows for a set of tooth shade guides to be stored in a holder 32, as shown in FIG. 6. These individual guides can also be custom stained in the mouth to more accurately achieve the desired result. Variations using internal layers of color modifiers or surface layers of color can be used.

While the invention has been disclosed and described with reference to a single embodiment of the invention, it will be apparent that changes and modifications may be made therein which falls within the true spirit and scope of the present invention as defined in the following claims.

What is claimed is:

1. A tooth shade guide comprising:
    a tooth shaped member having an open space adapted to receive a post or anchor in a patient's mouth; said tooth shaped member having a front surface, a rear surface, two curved opposite side surfaces connected between said front and rear surfaces and an occlusal surface connected to said front surface, said side surfaces and said rear surface; said front, rear, occlusal and side surfaces defining said open space; said open space having an opening opposite said occlusal surface for receiving said post or anchor into said open space; said front surface and said side surfaces having a specified shape, color and finish which replicates the appearance of the front and side surfaces of a corresponding artificial tooth such that when said tooth shaped member is positioned over a post or anchor in a patient's mouth the appropriate color can be selected for an artificial tooth;

said shade guide further including a substantially straight handle member extending rearwardly from said rear surface of said tooth shaped member.

2. A tooth shade guide as claimed in claim 1 wherein said front surface and said side surfaces of said tooth shaped member are constructed of superimposed layers having a base layer of metal, an intermediate layer of dentin, and an external layer of porcelain.

3. A tooth shade guide as claimed in claim 1 wherein said tooth shaped member has a color selected from a group of common colors of natural teeth.

* * * * *